(12) United States Patent
Cheung et al.

US006451995B1

(10) Patent No.: US 6,451,995 B1
(45) Date of Patent: Sep. 17, 2002

(54) SINGLE CHAIN FV POLYNUCLEOTIDE OR PEPTIDE CONSTRUCTS OF ANTI-GANGLIOSIDE $G_{D2}$ ANTIBODIES, CELLS EXPRESSING SAME AND RELATED METHODS

(75) Inventors: Nai-Kong V. Cheung, Purchase, NY (US); Steven M. Larson, Washington, DC (US); Hong-Fen Guo, New York, NY (US); Ken Rivlin, New York, NY (US); Michel Sadelain, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/142,974

(22) PCT Filed: Mar. 20, 1997

(86) PCT No.: PCT/US97/04427

§ 371 (c)(1),
(2), (4) Date: Sep. 18, 1998

(87) PCT Pub. No.: WO97/34634

PCT Pub. Date: Sep. 25, 1997

Related U.S. Application Data

(60) Provisional application No. 60/013,703, filed on Mar. 20, 1996.

(51) Int. Cl.⁷ .............................................. C12N 15/13
(52) U.S. Cl. ................................ 536/23.53; 530/387.3; 530/388.85
(58) Field of Search ............................. 536/23.1, 23.4, 536/23.53; 530/387.3, 388.85; 424/133.1, 134.1, 135.1, 178.1; 435/326, 328, 330, 4, 7.1

(56) References Cited

U.S. PATENT DOCUMENTS

| 4,675,287 A | | 6/1987 | Reisfeld et al. |
|---|---|---|---|
| 4,946,778 A | | 8/1990 | Ladner et al. |
| 5,302,370 A | | 4/1994 | Neumeier et al. |
| 5,359,046 A | | 10/1994 | Capon et al. |
| 5,405,990 A | | 4/1995 | Burke et al. |
| 5,540,926 A | * | 7/1996 | Aruffo et al. |
| 5,851,527 A | * | 12/1998 | Hansen |
| 5,965,371 A | * | 10/1999 | Marasco et al. |
| 5,973,116 A | * | 10/1999 | Epenetos et al. |

FOREIGN PATENT DOCUMENTS

| WO | WO 92/18629 | * | 10/1992 |
|---|---|---|---|
| WO | WO 93/19163 | * | 9/1993 |

OTHER PUBLICATIONS

Paul, Fundamental Immunology, Ravin Press NY, chapter 8, p. 242, 1993.*
Gillies et al., Proc. Natl. Acad. Sci. USA 89:1428–32, 1992.*
Huston et al., Proc. Natl. Acad. Sci. USA 85:5879–83, 1988.*

* cited by examiner

Primary Examiner—Sheela Huff
Assistant Examiner—Larry R. Helms
(74) Attorney, Agent, or Firm—Oppedahl & Larson LLP

(57) ABSTRACT

Recombinant antibody constructs comprise the variable regions of the heavy and light chains of anti-$G_{D2}$ antibodies. These antibody constructs may be coupled to a label such as a radiolabel or to a protein such as streptavidin or pro-drug converting enzymes for use in imaging or therapeutic applications. The antibody constructs may also be transduced into T cells to produce populations of T cells which target $G_{D2}$-producing tumor cells.

8 Claims, 1 Drawing Sheet

SEQUENCE LISTING

<160> NUMBER OF SEQ ID NOS: 5

<210> SEQ ID NO 1
<211> LENGTH: 717
<212> TYPE: DNA
<213> ORGANISM: Murine
<220> FEATURE:
<223> OTHER INFORMATION: 5F11-scFv
<221> NAME/KEY: unsure
<222> LOCATION: (37)
<221> NAME/KEY: unsure
<222> LOCATION: (79)

<400> SEQUENCE: 1

| | | | | |
|---|---|---|---|---|
| caggtgaaac | tgcagcagtc | aggacctgaa | ctggtgnagc | ctggggcttc agtgaagata | 60 |
| tcctgcaaga | cttctggana | caaattcact | gaatacacca | tgcactgggt gaagcagagc | 120 |
| catggaaaga | gccttgagtg | gattggaggt | attaatccta | caaatggtgg tactaactac | 180 |
| aagcagaagt | tcaagggcaa | ggccacattg | actgtagaca | agtcctccag cacagcctac | 240 |
| atggagctcc | gcagcctgac | atctgaggat | tctgcagtct | attactgtgc aagagatact | 300 |
| acggtcccgt | ttgcttactg | ggtccaaggg | accacggtca | ccgtctcctc aggtggaggc | 360 |
| ggttcaggcg | gaggtggctc | tggcggtggc | ggatcgaca | tcgagctcac tcagtctcca | 420 |
| gcaatcatgt | ctgcatctcc | aggggagaag | gtcaccatga | cctgcagtgg cagctcaagt | 480 |
| ataagttaca | tgcactggta | ccagcagaag | cctgtcacct | cccccaaaag atggatttat | 540 |
| gacacatcca | aactggcttc | tggagtccct | gctcgcttca | gtggcagtgg gtctgggacc | 600 |
| tcttattctc | tcacaatcag | cagcatggag | gctgtagatg | ctgccactta ttactgccat | 660 |
| cagcggagta | gttacccgct | cacgttcggt | gctgggacac | agttggaaat aaaacgg | 717 |

<210> SEQ ID NO 2
<211> LENGTH: 714
<212> TYPE: DNA
<213> ORGANISM: Murine
<220> FEATURE:
<223> OTHER INFORMATION: 3G6-scFv

<400> SEQUENCE: 2

| | | | | |
|---|---|---|---|---|
| agtattgtga | tgacccagac | tcccaaattc | ctgcttgtat | cagcaggaga cagggttacc | 60 |
| ataacctgca | aggccagtca | gagtgtgagt | aatgatgtgg | cttggtacca acagaagcca | 120 |
| gggcagtctc | cgaaactgct | gatatactct | gcatccaatc | gctacactgg agtccctgat | 180 |
| cgcttcactg | gcagtggata | tgggacggat | ttcactttca | ccatcagcac tgtgcaggct | 240 |
| gaagacctgg | cagtttattt | ctgtcagcag | gattatagct | cgctcggagg ggggaccaag | 300 |
| ctggaaataa | aagtggagg | cggttcaggc | ggaggtggct | ctggcggtgg cggatcgcag | 360 |
| gtgcaggtga | aggagtcagg | acctggcctg | gtggcgccct | cacagagcct gtccatcact | 420 |
| tgcactgtct | ctgggttttc | attaaccaat | tatggtgtac | actgggttcg ccagcctcca | 480 |
| ggaaagggtc | tggagtggct | gggagtaata | tgggctggtg | gaagcacaaa ttataattcg | 540 |
| gctcttatgt | ccagactgag | catcagcaag | gacaactcca | agagccaagt ttttcttaaaa | 600 |
| atgaacagtc | tgcaaactga | tgacacagcc | atgtactact | gtgccagtcg gggggtaac | 660 |
| tacggctatg | ctttggacta | ctggggtcaa | ggaacctcag | tcaccgtctc ctca | 714 |

<210> SEQ ID NO 3
<211> LENGTH: 1176

-continued

```
<212> TYPE: DNA
<213> ORGANISM: Murine
<220> FEATURE:
<223> OTHER INFORMATION: 5F11-scFv-streptavidin
<221> NAME/KEY: unsure
<222> LOCATION: (37)
<221> NAME/KEY: unsure
<222> LOCATION: (79)

<400> SEQUENCE: 3
caggtgaaac tgcagcagtc aggacctgaa ctggtgnagc ctggggcttc agtgaagata      60
tcctgcaaga cttctggana caaattcact gaatacacca tgcactgggt gaagcagagc     120
catggaaaga gccttgagtg gattggaggt attaatccta caatggtgg tactaactac      180
aagcagaagt tcaagggcaa ggccacattg actgtagaca agtcctccag cacagcctac     240
atggagctcc gcagcctgac atctgaggat tctgcagtct attactgtgc aagagatact     300
acggtcccgt ttgcttactg gtccaaggg accacggtca ccgtctcctc aggtggaggc      360
ggttcaggcg gaggtggctc tggcggtggc ggatcggaca tcgagctcac tcagtctcca     420
gcaatcatgt ctgcatctcc aggggagaag gtcaccatga cctgcagtgg cagctcaagt     480
ataagttaca tgcactggta ccagcagaag cctgtcacct cccccaaaag atggatttat     540
gacacatcca aactggcttc tggagtccct gctcgcttca gtggcagtgg gtctgggacc     600
tcttattctc tcacaatcag cagcatggag gctgtagatg ctgccactta ttactgccat     660
cagcggagta gttacccgct cacgttcggt gctgggacac agttggaaat aaaacgggcg     720
gccgctggat ccggtgctgc tgaagcaggt atcaccggca cctggtacaa ccagctcggc     780
tcgaccttca tcgtgaccgc gggcgccgac ggcgccctga ccggaaccta cgagtcggcc     840
gtcggcaacg ccgagagccg ctacgtcctg accggtcgtt acgacagcgc cccggccacc     900
gacggcagcg gcaccgccct cggttggacg gtggcctgga agaataacta ccgcaacgcc     960
cactccgcga ccacgtggag cggccagtac gtcggcggcg ccgaggcgag gatcaacacc    1020
cagtggctgc tgacctccgg cacaaccgag gccaacgcct ggaagtccac gctggtcggc    1080
cacgacacct tcaccaaggt gaagccgtcc gccgcctccg gatccgaaca aaagctgatc    1140
tcagaagaag atctatgcat acatcaccat catcat                              1176

<210> SEQ ID NO 4
<211> LENGTH: 1173
<212> TYPE: DNA
<213> ORGANISM: Murine
<220> FEATURE:
<223> OTHER INFORMATION: 3G6-scFv-streptavidin

<400> SEQUENCE: 4
agtattgtga tgacccagac tcccaaattc ctgcttgtat cagcaggaga cagggttacc      60
ataacctgca aggccagtca gagtgtgagt aatgatgtgg cttggtacca acagaagcca     120
ggcagtctc cgaaactgct gatatactct gcatccaatc gctacactgg agtccctgat      180
cgcttcactg gcagtggata tgggacggat ttcactttca ccatcagcac tgtgcaggct     240
gaagacctgg cagtttattt ctgtcagcag gattatagct cgctcggagg ggggaccaag     300
ctggaaataa aagtggagg cggttcaggc ggaggtggct ctggcggtgg cggatcgcag      360
gtgcaggtga aggagtcagg acctggcctg gtggcgccct cacagagcct gtccatcact     420
tgcactgtct ctgggttttc attaaccaat tatggtgtac actgggttcg ccagcctcca     480
ggaaagggtc tggagtggct gggagtaata tgggctggtg aagcacaaa ttataattcg      540
```

-continued

| | | | | |
|---|---|---|---|---|
| gctcttatgt | ccagactgag | catcagcaag | gacaactcca | agagccaagt tttcttaaaa | 600 |
| atgaacagtc | tgcaaactga | tgacacagcc | atgtactact | gtgccagtcg gggggtaac | 660 |
| tacggctatg | ctttggacta | ctggggtcaa | ggaacctcag | tcaccgtctc ctcagcggcc | 720 |
| gctggatccg | gtgctgctga | agcaggtatc | accggcacct | ggtacaacca gctcggctcg | 780 |
| accttcatcg | tgaccgcggg | cgccgacggc | gccctgaccg | gaacctacga gtcggccgtc | 840 |
| ggcaacgccg | agagccgcta | cgtcctgacc | ggtcgttacg | acagcgcccc ggccaccgac | 900 |
| ggcagcggca | ccgccctcgg | ttggacggtg | gcctggaaga | ataactaccg caacgcccac | 960 |
| tccgcgacca | cgtggagcgg | ccagtacgtc | ggcggcgccg | aggcgaggat caacacccag | 1020 |
| tggctgctga | cctccggcac | aaccgaggcc | aacgcctgga | agtccacgct ggtcggccac | 1080 |
| gacaccttca | ccaaggtgaa | gccgtccgcc | gcctccggat | ccgaacaaaa gctgatctca | 1140 |
| gaagaagatc | tatgcataca | tcaccatcat | cat | | 1173 |

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: antibody tag

<400> SEQUENCE: 5

Gly Ala Pro Val Pro Val Pro Asp Pro Leu Glu Pro Arg
 1               5                  10

SINGLE CHAIN FV POLYNUCLEOTIDE OR PEPTIDE CONSTRUCTS OF ANTI-GANGLIOSIDE $G_{D2}$ ANTIBODIES, CELLS EXPRESSING SAME AND RELATED METHODS

This application is a national phase application under 35 USC §371 of PCT/US97/04427, filed Mar. 20, 1997, and claims priority therefrom and from the U.S. Provisional Application, Serial No. 60/013,703, filed Mar. 20, 1996, upon which the PCT application was based.

BACKGROUND OF THE INVENTION

This application relates to single chain antibody constructs which specifically bind to the disialoganglioside $G_{D2}$, and to the use of such constructs for targeted delivery of imaging agents or therapeutic agents to human neuroectodermal derived cancers.

Gangliosides are acidic glycosphingolipids found on the outer surface of most cell membranes.[1] Many tumors have abnormal glycolipid composition and structure. Disialoganglioside $G_{D2}$ has been found in a wide spectrum of human tumors, including neuroblastoma, osteosarcomas and other soft tissue sarcomas, medulloblastomas, high grade astrocytomas, melanomas, and small cell lung cancer.[2-4] Among glioblastoma multiforme and anaplastic astrocytoma, anti-$G_{D2}$ demonstrated the most restrictive pattern when compared with anti-$G_{D3}$ and anti-GM2 antibodies.[5,6]

Gangliosides are ideal targets for monoclonal antibodies (MAb) because of the high antigen density, lack of modulation, relative homogeneity in many tumors and the possibility of up-regulation by cytokines.[7] The only normal tissues with high ganglioside expression are neurons, and biodistribution studies have shown that MAb do not localize to the nontumorous brain or spinal cord because of the blood brain barrier. In contrast, in patients with primary or metastatic brain tumors, specific antibodies can localize preferentially to tumor tissues, but not to normal brain.[8]

Murine monoclonal antibodies have been prepared to ganglioside $G_{D2}$. Using somatic cell hybridization, murine MAbs were produced against the ganglioside $G_{D2}$.[9] They were shown to react with disialoganglioside $G_{D2}$, but not with GD3, GT1b, GD1b, GD1a, GM1, GM3 and GM4. When base-treatment step was omitted from the standard neuroblastoma ganglioside extraction procedure, immuno-thin-layer-chromatography (ITLC) using 3F8, 3G6 and other anti-$G_{D2}$ MAbs revealed a new ganglioside band with Rf of 0.342, besides $G_{D2}$ (Rf 0.183).[4] Immunochemical analysis showed that this new neuroblastoma ganglioside contained alkali-sensitive O-acetylated sialic acid residues recognized by MAb D1.1.

Of 15 anti-$G_{D2}$ MAbs studied, 13 reacted strongly with the novel ganglioside. 3F8 was chosen for our initial clinical studies because of its being an IgG3 and its strong binding in vitro to $G_{D2}$. Based on the cDNA sequence and the anti-idiotype cross-reactivity, the antigen specificity and affinity of 3f8 and 3G6 were similar if not identical. We have chosen 3G6 for scFv development for ease of comparison with the other 14 MAbs which are IgM antibodies.

TABLE 1

SPECIFICITY OF ANTI-$G_{D2}$ MAb.

| MAb  | $G_{D2}$ | GD3 | "O-$G_{D2}$" | GD1b |
|------|----------|-----|--------------|------|
| 1A8  | 4+       | −   | ±            | 1+   |
| 1F9  | 4+       | ±   | 3+           | 1+   |
| 1H12 | 4+       | ±   | 3+           | 1+   |
| 2F7  | 3+       | −   | 1+           | −    |
| 3A7  | 3+       | −   | −            | −    |
| 3A10 | 4+       | 1+  | 2+           | 1+   |
| 3B4  | 4+       | −   | 3+           | 1+   |
| 3F8  | 4+       | −   | 4+           | −    |
| 3G6  | 4+       | −   | 2+           | −    |
| 4C11 | 4+       | −   | 3+           | ±    |
| 5E11 | 4+       | −   | 4+           | −    |
| 5F4  | 4+       | 1+  | 2+           | 1+   |
| 5F11 | 2+       | ±   | 3+           | 1+   |
| 6E8  | 4+       | 1+  | 3+           | 1+   |
| 6H4  | 4+       | ±   | 3+           | 1+   |

"O-$G_{D2}$", a novel neuroblastoma alkali-labile ganglioside band consistent with the O-acetylated form of disialoganglioside $G_{D2}$.
4+ = deep, dark staining band;
3+ = dark staining;
2+ = clearly staining;
1+ = faint staining;
± = very faint staining;
− = negative.
All MAbs were tested negative to $G_{M1}$, $G_{M3}$, $G_{D1a}$ AND $G_{T1b}$.

In order to determine the general applicability of the ganglioside $G_{D2}$ as a target for immunotherapy, its expression in human cancers has been studied by immunostaining tumor specimens using these monoclonal antibodies. These anti-$G_{D2}$ antibodies reacted with all the neuroblastoma surgical specimens tested to date in our laboratory. A recent update[10] analyzed a series of 39 neuroblastomas. Staining of both primitive neuroblastic and differentiating ganglioneuromatous elements were seen, although tumor cell heterogeneity was noted in some. 23/39 tumors showed a more intense reactivity with MAb 3A7 than with 3F8, and this was particularly evident in the primitive neuroblastoma group. In a separate study, the expression of $G_{D2}$ was analyzed in 67 solid tumors and normal tissues from children by using the antibody 3A7.[11] $G_{D2}$ expression was found in 28 of 28 neuroblastomas, and was most abundant in stroma-poor tumors. Differentiating stroma-rich neuroblastomas, neuroblastic clusters, neurofibrils, and most ganglion-like cells were found to be $G_{D2}$ positive, whereas Schwann's-cell stroma did not express $G_{D2}$. In ganglioneuromas, only a few ganglion-like cells showed $GD_2$, whereas all other structures were negative. Scattered foci of $G_{D2}$ were also found in some non-neuronal tumors, such as rhabdomyosarcomas and osteosarcomas, but not in lymphomas, Askin tumors, or most Wilm's tumors. 3A7 was also found to react with retinoblastomas.[12]

Previous studies have shown that anti-$G_{D2}$ antibodies reacted with the majority of osteosarcomas.[13] Sixty freshly frozen human soft-tissue sarcomas were studied by avidin-biotin immunostaining using purified monoclonal antibodies 3F8 (anti-$G_{D2}$) and R24 (anti-GD3).[14] Ninety-three percent of the tumors tested by the immunohistochemical staining expressed $G_{D2}$ and 88% expressed GD3. The intensity of expression varied among different histologic types. Liposarcoma, fibrosarcoma, malignant fibrous histiocytoma, leiomyosarcoma and spindle cell sarcoma reacted strongly with both antibodies. Embryonal rhabdomyosarcoma and synovial sarcoma demonstrated substantially weaker staining by either MAb. Ganglioside extraction and immuno-thin layer chromatography (ITLC) confirmed the identities of these gangliosides as $G_{D2}$ and GD3 respectively.

Among brain tumors, 3F8 and 3A7 have also shown excellent reactivities. Two separate studies were carried out the first study in collaboration with Dr. Paul Zeltzer of Texas and the second with Dr. Ira Bergman (now Associate Professor of Neurology at the University of Pittsburgh) in our laboratory. In the first study, 12/15 medulloblastoma and 16/18 astrocytoma were positive, the majority staining homogeneously. In the second study, similar results were obtained. Medulloblastoma and a number of brain tumors reacted strongly with 3F8 and 3A7. The pattern of reactivity was generally homogeneous. For small cell lung cancer, all have reacted homogeneously in vitro using immunoperoxidase techniques.

Despite in vitro evidence for exquisite specificity of these antibodies for the ganglioside $G_{D2}$ on neuroblastoma cells, a critical test of in vivo delivery is the actual amount of MAb uptake in the tumors. Biodistribution of 131I-anti-$G_{D2}$ antibody was tested in preclinical experiments using athymic mice xenografted with human neuroblastoma.

Between 8 to 50% injected dose of 131I-MAb/gm of tumor was found, with variability depending primarily on the size of the tumor.[15] There was no localization to $G_{D2}$-negative tumors like Ewing's sarcoma. Pooled mouse IgG and an irrelevant MAb also did not localize to neuroblastoma xenografts. Both small tumors (50 mg) and large tumors (over 2 g) showed radiolocalization with this technique. Optimal tumor to normal tissue ratios were rapidly reached by 24 to 48 hours. There was no increased uptake in the reticuloendothelial system, and the MAb did not cross the intact blood-brain barrier. The efficacy of tumor targeting was then tested by imaging neuroblastoma patients with 131I-MAb. Radiolocalization was demonstrated in primary tumors of the mediastinum and abdomen, as well as metastatic disease in the lymph nodes, bone marrow and bone.[61,17] The specificity was validated by tumor and marrow biopsies, as well as by CT/MRI and bone scans. A comparison with 131I-meta-iodobenzylguanidine (MIBG) suggested that 131I-MAb was twice as sensitive in detecting metastatic sites of disease. The tumor uptake in patients was 0.08% of the injected dose per gm (compared to 0.002% for MIBG). This high tumor uptake in vivo was a result of (1) the high density (5×106/cell) and homogeneity of the target antigen $G_{D2}$, and (2) the lack of uptake in the reticuloendothelial system. A number of human cancers has been imaged using $G_{D2}$ specific antibodies. These include small cell lung cancer,[18] brain tumors,[8] and both osteosarcomas[13] and soft tissue sarcomas.[19]

A phase I study to test the biological toxicity of "cold" anti-$G_{D2}$ was carried out in 1987 in 17 patients with metastatic neuroblastoma or melanoma. A subsequent phase II study was carried out in 16 patients with stage IV neuroblastoma. Acute self-limited toxicities of MAb treatment were severe pain requiring analgesics, fever, urticaria, hypertension, hypotension, anaphylactoid reactions of the respiratory tract, as well as significant decreases in blood counts and serum complement levels. There were no treatment related deaths. Among the 5 neuroblastoma patients who are still alive and well (19 mos, 3 y, 5 y, 5 y, 6 y respectively after MAb treatment), there are no acute or delayed neurological complications attributable to MAb therapy. Among the survivors, one patient had chemoradiotherapy-resistant stage IVS neuroblastoma, and the other 4 had poor risk stage IV neuroblastoma diagnosed at more than one year of age (2 relapsed neuroblastoma and 2 with refractory neuroblastoma prior to antibody treatment).

More recently, a phase I study to determine the radiological toxicity was carried out. Twenty-three patients (11 M and 21 F, ranging from 0.3 to 24.2 years of age at diagnosis) with refractory neuroblastoma (22 stage IV, 1 stage IIIU), were treated with 131I-3F8 at 7 dose levels, namely 6, 8, 12, 16, 20, 24, and 28 mCi/kg. Radiation dose to the blood was calculated based on blood clearance total body dose was based on total body clearance, and the tumor/organ dose on regions of interest calculations from serial gamma imagings. 21/23 patients were rescued with autologous bone marrow; one patient received GM-CSF alone; one died of progressive disease before marrow reinfusion. Marrow was infused when blood radioactivity decreased to <0.01 uCi/ml in the first 18 patients and to <1 uCi/ml in the last 4 patients. Acute toxicities of 131I-MAb treatment included pain (19/23) during the infusion, fever (19/23), hyperbilirubinemia (6/23), and diarrhea. All patients developed grade 4 myelosuppression with sepsis in 7/23 patients (5 fungal, 2 bacterial), disseminated zoster in 1, and pneumocystis in 1. Despite orally administered saturated solution of potassium iodide, 3 patients developed hypothyroidism. Subsequent 14 patients were treated with synthroid or Cytomel for thyroid protection. No other significant extramedullary toxicities have been encountered in patients followed past 20 months (50+, 40+, 30+, 26+, 23+, mos) from the time of 131I-MAb treatment. Fourteen patients have died, 11 of disease and 3 from infections during the cytopenic period, and in 4 patients follow-up is still short. Responses were seen in both soft tissue masses and bone marrow. Average tumor dose was 150 rad/mCi/kg. We concluded that when 131I-MAb was administered intravenously (6–28 mCi/kg), significant toxicities were encountered, including myelosuppression and their infectious complications, pain, fever, as well as hypothyroidism. Autologous marrow rescue could reverse marrow aplasia and thyroid supplement was essential to prevent thyroid damage. Although severe extramedullary toxicities were not seen, improvement in the pharmacokinetics of the radioconjugates will reduce significantly the marrow toxicity.

To date, a total of >95 patients have been treated with antibody 3F8, and more than 120 imaging studies have been carried out on different ongoing protocols. Among pediatric patients, no neuropathy has been reported, either sensory or motor in nature. More than two thirds of these patients mounted HAMA response, mostly low titer and not persistent. There was no correlation of HAMA with toxicity. Nevertheless, in view of the neuropathy seen with other anti-$G_{D2}$ antibodies 14.2a and 14.18 (similar in reactivity patterns to 3F8), we want to improve the specificity to reduce side effects. All of these clinical trials have been carried out using antibodies produced at Memorial Sloan-Kettering Cancer Center using guidelines of the Office of Biologics Research and Review Center for Drugs and Biologics, Food and Drug Administration. For quality assurance, hybridoma 3F8 was found to be negative for adventitious agents by MAP, S+L-, and XC plaque assays, as well as negative for reverse transcriptase. MAP testing included screening for murine leukovirus, LCM virus isolation by intracerebral inoculation, murine saliva gland virus, mouse thymic virus, EDIM and LDH virus isolations. Purified antibody (e.g. 3F8) had to pass MAP and sterility testing (bacteria, mycoplasma, and fungal cultures), rabbit pyrogen testing, as well as safety testing in mice and guinea pigs. Conjugation to 131I by the chloramine-T method was supervised by Dr. Ronald Finn and Dr. Steven Larson in the Department of Nuclear Medicine. Specific activity of iodine-131 was >600 mCi/ug iodide. Radiolabeled antibody 3F8 must have >50% binding by in vitro antigen binding assay, >95% TCA precipitable and <3% free iodine by radio-thin layer chromatography. Periodic testing of radio-labeled antibodies was performed to ensure sterility as well as the absence of pyrogen.

Although the wide expression of $G_{D2}$ in human neuroectodermal-derived cancers (melanoma, small cell lung cancer, neuroblastoma, brain tumors, sarcoma, HTLV-1 leukemia, retinoblastoma and osteosarcoma) and the preliminary clinical studies of monoclonal antibodies to $G_{D2}$ in radioimmuno-scintigraphy and radioimmunotherapy have been encouraging, further optimization of antibodies for binding to $G_{D2}$ would be desirable. It is an object of the present invention to provide such optimized antibodies and the DNA sequences coding therefore.

It is a further object of the invention to provide methods of using the optimized antibodies and DNA sequences in diagnostic assays and therapeutic techniques.

SUMMARY OF THE INVENTION

The antibodies of the present invention are recombinant antibody constructs comprising the variable regions of the heavy and light chains of anti-$G_{D2}$ antibodies. These antibody constructs may be coupled to a label such as a radiolabel or to a protein such as streptavidin or pro-drug converting enzymes for use in imaging or therapeutic applications. The antibody constructs may also be transduced into T cells to produce populations of T cells which target $G_{D2}$-producing tumor cells.

DETAILED DESCRIPTION OF THE INVENTION

Figure 1:
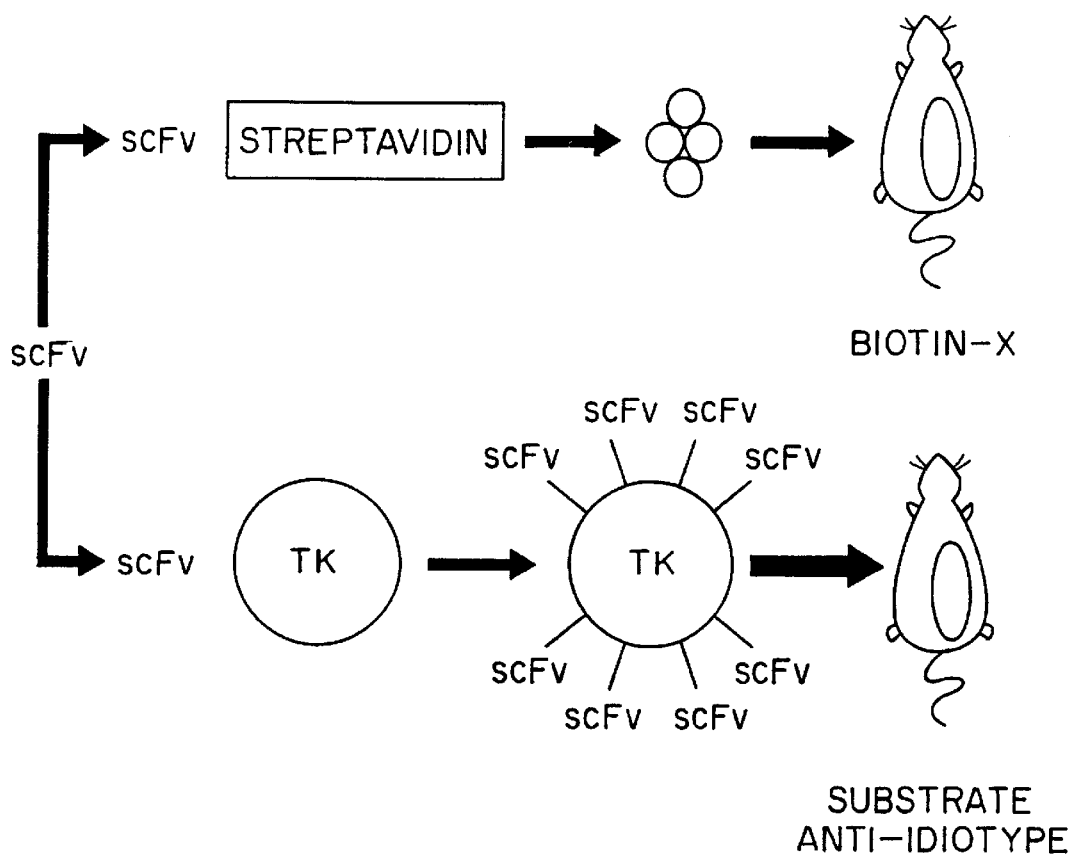
FIG. 1 shows two alternative strategies for the use of the antibody constructs of the present invention in therapy.

This invention relates to optimized antibodies to $G_{D2}$, to DNA encoding such antibodies, and to the use of the antibodies and DNA in diagnostic assays and therapy. The antibodies of the invention are antibody constructs comprising the variable regions of the heavy and light chains of anti-$G_{D2}$ antibodies as a single chain Fv fragment. Single-chain Fv fragments (scFv) offer some of the best opportunities to achieve these results. ScFv technology utilizes molecular biology methods to reduce antibodies to the minimal-required-unit of heavy and light chain variable regions tethered by a peptide linker which can be designed with versatile side chains for radioconjugation.

The anti-$G_{D2}$ scFvs shown in Tables 2 and 3 have been prepared using the methods described in the examples. For 5F11 the orientation VH-VL is used for the scFv. For 3G6 the orientation VL-VH is necessary. Since the cDNA sequences of 3G6 and 3F8 are similar, we expect the binding properties of both of these antibodies to be very similar if not identical. Since our cloning strategies have been most successful with 3G6, this has been the focus of our research instead of 3F8. Histidine-tag (His5) is inserted for ease of purification by Ni-column and Myc-tag is inserted to facilitate detection. Myc-tag and E-tag can be genetically removed if necessary for future clinical studies. These svFv variants were constructed to test the effect of (1) the detection-tag (E-tag or Myc-tag), (2) the presence of His5-tag, and (3) the position of His5-tag (carboxyl-end-terminal versus internal) on (a) antibody specificity, (b) affinity, and (c) ease of purification.

In order to increase the avidity of the scFv, we have synthesized two scFv variants: (1) Cysteine residue at the carboxyl terminal of the scFv for dimerization (5FpoMCH of Table 2 and 3GpoMCH of Table 3): Free sulhydryl groups are blocked by acetylation and the monomer separated from the dimer by size-exclusion chromatography FPLC on Sephadex HR75 (Pharmacia). (2) Streptavidin at the carboxyl end for dimerization and tetramerization (5FpoStMCH of table 1 and 3GpoStMCH of table 2): Streptavidin is a homo-tetrameric protein that binds one biotin molecule per subunit with a very high affinity (Kd= $4 \times 10-14$). scFv-strep fusion proteins are expected to form tetramers with both antigen- and biotin-binding activity. They are expected to be stable over a wide range of pH and range of physiologic temperatures.

TABLE 2

| scFv Expression Vector | 5FpcHE pCantab | 5FphM pHEN | 5FphHM pHEN | 5FpoMCH pOPE | 5FpoStMCH* pOPE |
|---|---|---|---|---|---|
| Tag |  |  |  |  |  |
| E-tag | + | − | − | − | − |
| Myc-tag | − | + | + | + | + |
| His-tag | + | − | + | + | + |
| Bacteria Host |  |  |  |  |  |
| phagemid | XL1-blue | XL1-blue | XL1-blue | − | − |
| phage | hb2151 | hb2151 | hb2151 | JM109 | JM109 |
| Restriction sites: |  |  |  |  |  |
| 5' Nco1 | − | + | + | − | − |
| 5' PvuII | − | − | − | + | + |
| 5' Sfil | + | − | − | − | − |
| 3' NOT1 | + | + | + | + | + |
| Binding** |  |  |  |  |  |
| $G_{D2}$ elisa | + | + | + | + | + |
| ITLC | + | + | + | + | + |
| Western blot** | + | + | + | + | + |
| Purification | nd | nd | nd | + | + |

*5F = 5F11 hybridona of origin
pc = pCantab expreseion
ph = pHEN expression vector
po = vector constructed for optimal protein expression (Dubel et al)
E = E-tag (for detection)
H = histidine-tag (For purification)
M = myc-tag (for detection)
C = cysteine residue (For dimerization)
**ITLC = immuno-thin-layer-chromatography, + = positive binding to $G_{D2}$ (Elisa or ITLC) or to anti-myc (Western blot)

TABLE 3

| scFv Expression Vector | 3GphM pHEN | 3GphHM pHEN | 3GpOMCH pOPE | 3GpoStMCH* pOPE |
|---|---|---|---|---|
| Tag |  |  |  |  |
| E-tag | − | − | − | ± |
| Myc-tag | + | + | + | + |
| His-tag | − | + | + | + |
| Bacteria Host |  |  |  |  |
| phagemid | XL1-blue | XL1-blue | − | − |
| phage | hb2151 | hb2151 | JM109 | JM109 |
| Restriction sites: |  |  |  |  |
| 5' Nco1 | + | + | + | + |
| 5' Sfil | − | − | − | − |
| 3' NOT1 | + | + | + | + |

TABLE 3-continued

| scFv Expression Vector | 3GphM pHEN | 3GphHM pHEN | 3GpOMCH pOPE | 3GpoStMCH* pOPE |
|---|---|---|---|---|
| Binding** | | | | |
| G$_{D2}$ elisa | + | + | + | + |
| ITLC | nd | nd | + | nd |
| anti-id | nd | nd | + | nd |
| Western blot** | + | + | + | + |
| Purification | nd | nd | + | nd |

*3G = 3G6 hybridona of origin
ph = pHEN expression vector
po = Vector constructed for optimal protein expression (Dubel et al)
E = E-tag (for detection)
H = histidine-tag (For purification)
M = myc-tag (for detection)
C = cysteine residue (For dimerization)
** ITLC = immuno-thin-layer-chromatography, + = positive binding to G$_{D2}$ (Elisa or ITLC) or to anti-myc (Western blot)

The 5F11-scFv, 3G6-scFv, 5F11-scFv-streptavidin, 3G6-scFv-streptavidin DNA sequences are shown below, with the linker sequences between the scFv and the streptavidin shown in lower case letters.

5F11-svFv (SEQ ID NO. 1) CAGGTGAAACTGCAGCAGTCAGGACCTGAACTGGTGNAGCCTGGGGCTTCAG TGAAGATATCCTGCAAGACTTCTGGANACAAATTCACTGAATACACCATGCAC TGGGTGAAGCAGAGCCATGGAAAGAGCCTTGAGTGGATTGGAGGTATTAAT CCTAACAATGGTGGTACTAACTACAAGCAGAAGTCAAGGGCAAGGCCACAT TGACTGTAGACAAGTCCTCCAGCACAGCCTACATGGAGCTCCGCAGCCTGAC ATCTGAGGATTCTGCAGTCTATTACTGTGCAAGAGATACTACGGTCCCGTTTG CTTACTGGGTCCAAGGGACCACGGTCACCGTCTCCTCAGGTGGAGGCGGTTC AGGCGGAGGTGGCTCTGGCGGTGGCGGATCGGACATCGAGCTCACTCAGTCT CCAGCAATCATGTCTGCATCTCCAGGGGAGAAGGTCACCATGACCTGCAGTG GCAGCTCAAGTATAAGTTACATGCACTGGTACCAGCAGAAGCCTGTCACCTCC CCCAAAAGATGGATTTATGACACATCCAAACTGGCTTCTGGAGTCCCTGCTCG CTTCAGTGGCAGTGGGTCTGGGACCTCTTATTCTCTCACAATCAGCAGCATGG AGGCTGTAGATGCTGCCACTTATTACTGCCATCAGCGGAGTAGTTACCCGCTC ACGTTCGGTGCTGGGACACAGTTGGAAATAAAACGG

3G6-scFv (SEQ ID NO. 2) AGTATTGTGATGACCCAGACTCCCAAATTCCTGCTTGTATCAGCAGGAGACAG GGTTACCATAACCTGCAAGGCCAGTCAGAGTGTGAGTAATGATGTGGCTTGG TACCAACAGAAGCCAGGGCAGTCTCCGAAACTGCTGATATACTCTGCATCCAA TCGCTACACTGGAGTCCCTGATCGCTTCACTGGCAGTGGATATGGGACGGAT TTCACTTTCACCATCAGCACTGTGCAGGCTGAAGACCTGGCAGTTTATTTCTG TCAGCAGGATTATAGCTCGCTCGGAGGGGGGACCAAGCTGGAAATAAAAGG TGGAGGCGGTTCAGGCGGAGGTGGCTCTGGCGGTGGCGGATCGCAGGTGCA GGT-GAAGGAGTCAGGACCTGGCCTGGTGGCGCCCTCACAGAGCCTGTCCATC ACTTGCACTGTCTCTGGGTTTTCATTAACCAATTATGGTGTACACTGGGTTCG CCAGCCTCCAGGAAAGGGTCTGGAGTGGCTGGGAGTAATATGGGCTGGTGG AAGCACAAATTATAATTCGGCTCTTATGTCCAGACTGAGCATCAGCAAGGACA ACTCCAAGAGCCAAGTTTTCTTAAAAATGAACAGTCTGCAAACTGATGACACA GCCATGTACTACTGTGCCAGTCGGGGGGGTAACTACGGCTATGCTTTGGACT ACTGGGGTCAAGGAACCTCAGTCACCGTCTCCTCA

5F11-scFv-Streptavidin (SEQ ID NO. 3) CAGGTGAAACTGCAGCAGTCAGGACCTGAACTGGTGNAGCCTGGGGCTTCAG TGAAGATATCCTGCAAGACTTCTGGANACAAATTCACTGAATACACCATGCAC TGGGTGAAGCAGAGCCATGGAAAGAGCCTTGAGTGGATTGGAGGTATTAAT CCTAACAATGGTGGTACTAACTACAAGCAGAAGTCAAGGGCAAGGCCACAT TGACTGTAGACAAGTCCTCCAGCACAGCCTACATGGAGCTCCGCAGCCTGAC ATCTGAGGATTCTGCAGTCTATTACTGTGCAAGAGATACTACGGTCCCGTTTG CTTACTGGGTCCAAGGGACCACGGTCACCGTCTCCTCAGGTGGAGGCGGTTC AGGCGGAGGTGGCTCTGGCGGTGGCGGATCGGACATCGAGCTCACTCAGTCT CCAGCAATCATGTCTGCATCTCCAGGGGAGAAGGTCACCATGACCTGCAGTG GCAGCTCAAGTATAAGTTACATGCACTGGTACCAGCAGAAGCCTGTCACCTCC CCCAAAAGATGGATTTATGACACATCCAAACTGGCTTCTGGAGTCCCTGCTCG CTTCAGTGGCAGTGGGTCTGGGACCTCTTATTCTCTCACAATCAGCAGCATGG AGGCTGTAGATGCTGCCACTTATTACTGCCATCAGCGGAGTAGTTACCCGCTC ACGTTCGGTGCTGGGACACAGTTGGAAATAAAACGGgcggccgctggatccggtgctgct GAAGCAGGTATCACCGGCACCTGGTACAACCAGCTCGGCTCGACCTTCATCGT GACCGCGGGCGCCGACGGCGCCCTGACCGGAACCTACGAGTCGGCCGTCGG CAACGCCGAGAGCCGCTACGTCCTGACCGGTCGTACGACAGCGCCCCGGCC ACCGACGGCAGCGGCACCGCCCTCGGTTGGACGGTGGCCTGGAAGAATAACT ACCGCAACGCCCACTCCGCGACCACGTGGAGCGGCCAGTACGTCGGCGGCGC CGAGGCGAGGATCAACACCCAGTGGCTGCTGACCTCCGGCACAACCGAGGCC AACGCCTGGAAGTCCACGCTGGTCGGCCACGACACCTTCACCAAGGTGAAGC CGTCCGCCGCCTCCGGATCCGAACAAAAGCTGATCTCAGAAGAAGATCTATG CATACATCACCATCATCAT 3G6-scFv-streptavidin (SEQ ID NO. 4) AGTATTGTGATGACCCAGACTCCCAAATTCCTGCTTGTATCAGCAGGAGACAG GGTTACCATAACCTGCAAGGCCAGTCAGAGTGTGAGTAATGATGTGGCTv TGG TACCAACAGAAGCCAGGGCAGTCTCCGAAACTGCTGATATACTCTGCATCCAA TCGCTACACTGGAGTCCCTGATCGCTTCACTGGCAGTGGATATGGGACGGAT TTCACTTTCACCATCAGCACTGTGCAG-

```
GCTGAAGACCTGGCAGTTTATTTCTG TCAGCAG-
GATTATAGCTCGCTCGGAGGGGGGAC-
CAAGCTGGAAATAAAAGG
TGGAGGCGGTTCAGGCGGAGGTG-
GCTCTGGCGGTGGCGGATCGCAGGTGCA GGT-
GAAGGAGTCAGGACCTGGCCTGGTG-
GCGCCCTCACAGAGCCTGTCCATC
ACTTGCACTGTCTCTGGGTTTTCAT-
TAACCAATTATGGTGTACACTGGGTTCG CCAGC-
CTCCAGGAAAGGGTCTGGAGTGGCTGG-
GAGTAATATGGGCTGGTGG
AAGCACAAATTATAATTCGGCTCTTAT-
GTCCAGACTGAGCATCAGCAAGGACA ACTCCAA-
GAGCCAAGTTTTCTTAAAAATGAA-
CAGTCTGCAAACTGATGACACA
GCCATGTACTACTGTGC-
CAGTCGGGGGGTAACTACGGCTATGCTTTGGACT
ACTGGGGTCAAGGAACCTCAGTCAC-
CGTCTCCTCAgcggccgctggatccggtgctgctGAA GCAGG-
TATCACCGGCACCTGGTACAAC-
CAGCTCGGCTCGACCTTCATCGTGAC
CGCGGGCGCCGACGGCGCCCTGACCG-
GAACCTACGAGTCGGCCGTCGGCAAC
GCCGAGAGCCGCTACGTCCTGACCG-
GTCGTTACGACAGCGCCCGGCCACCG ACG-
GCAGCGGCACCGCCCTCGGTTGGACG-
GTGGCCTGGAAGAATAACTACCG
CAACGCCCACTCCGCGACCACGTG-
GAGCGGCCAGTACGTCGGCGGCGCCGAG GCGAG-
GATCAACACCCAGTGGCTGCTGACCTC-
CGGCACAACCGAGGCCAACG
CCTGGAAGTCCACGCTGGTCGGCCACGA-
CACCTTCACCAAGGTGAAGCCGTC CGCCGCCTC-
CGGATCCGAACAAAAGCTGATCTCAGAA-
GAAGATCTATGCATA CATCACCATCATCAT
```

All these single chains have strings of 5 histidine residues inserted at the carboxyl end for purification on the Nickel-column using FPLC. Washing was done at 10 mM Imidazole and scFv peak elution at 500 mM Imidazole. Further purification of scFv can be accomplished by size-exclusion using Sephadex HR75 and superose 6 (hi-resolution). scFv can be further affinity purified by myc-affinity chromatography. 9E10 is a hydridoma (ATCC) that secretes the antibody specific for the myc-tag. From ascites the 9E10 IgG1 antibody is purified by protein-G affinity chromatography and used for chemical coupling to sepharose 4B.

Recombinant antibody constructs according to the invention can be coupled to metal labels such as $^{99m}$Tc for use in diagnostic imaging of $G_{D2}$ expressing cells. For example, technetium can be chelated to the antibody construct via a heterobifunctional linker such as succinimidyl-6-hydrazinonicotinate hydrochloride (SHNH). SHNH is used to synthesize hydrazino-modified antibody. At a conjugation ratio of 1.8:1 of SHNH to antibody, immunoreactivity was preserved. Tc(V) precursors coupled readily and conveniently to the SHNH-modified protein to yield the desired 99mTc-radiolabeled conjugate. 99mTc-3F8 localized rapidly and successfully to $G_{D2}$-positive xenografts. SHNH-modified scFvs can be synthesized for conjugation to 99mTc using the techniques described in Schwartz et al., *Bioconjugate Chem* 2:333–336 (1991), which is incorporated herein by reference.

Metal chelation to scFv can also be accomplished via the streptavidin protein. The rationale of pretargeting using scFv-streptavidin fusion proteins in radioimmunotherapy are 5-fold: (a) Large amounts of scFv can be used to saturate $G_{D2}$ sites in vivo, without the accompanying blood and tissue toxicity from radioisotope, (b) radiolabel is injected at the time when the tumor-nontumor ratio of scFv is maximal, (c) a radiolabeled ligand is chosen such that it binds with high affinity (e.g. 111I-biotin binding to streptavidin) with fast blood-clearance, (d) a ligand construction where the isotope can be modified to optimize microdosimetry (e.g. SHNH-biotin) (e) the scFv-streptavidin is a homo-tetramer, as such the antigen binding avidity is greatly amplified especially for high-density antigens (e.g. $G_{D2}$ on neuroblastoma). scFv-strep fusion proteins for both 5F11 and 3G6 have been made and purified. Both in vitro and in vivo studies are being carried out to test the concept of pretargeting, where scFv-strep is first allowed to bind (or target) to $G_{D2}$-positive tumors through the scFv. After the excess or nonbinding scFv-strep is washed off (or cleared from the body), a radiolabeled-biotin ligand is allowed to bind to the streptavidin moiety. Different radiolabels can be coupled to biotin using SHNH ($^{99m}$Tc) or DTPA ($^{111}$In or yttrium).

scFv coupled to technetium provides a safe, camera-ready isotope, with fast-decay and therefore easy disposal. $^{99m}$-technetium is optimal for imaging studies. Other isotopes can also be used, including a positron-emitting technetium for PET imaging. Through the same side chain SHNH, rhenium (a therapeutic beta-emitting radionuclide) may also be attached.

The scFv and scFv-streptavidin of the invention are also useful in a number of therapeutic applications, which is turn form aspects of the present invention. In general, these approaches involve administration of scFV coupled to a therapeutic or pre-therapeutic moiety. For example, as shown in FIG. 1, ScFv-streptavidin (streptavidin being the pre-therapeutic moiety) is introduced into an organism suspected of harboring $G_{D2}$ expressing cells, where it binds to any such cells present. A therapeutic agent (X) bound to biotin is then introduced. Binding of the biotin the streptavidin results in localization of the chemotherapeutic agent X at the site of the $G_{D2}$ producing cells. Other pre-therapeutic moieties include pro-drug converting enzymes. Directly therapeutic moieties such as toxins can also be used.

A second approach, also illustrated in FIG. 1, utilizes a vector encoding ScFv is transduced into primary human lymphocytes (preferably along with a suicide gene such a HSV-TK). The transduced lymphocytes now recognize and target $G_{D2}$, resulting in an immune response to the $G_{D2}$-producing cells.

The scFv or scFv-streptavidin can be incorporated in a fusion protein with therapeutic agents such as toxins or pro-drug converting enzymes, can be incorporated in a fusion protein with CD8 to facilitate the formation of $G_{D2}$-targeted lymphocytes, or can be coupled to viral coat proteins superantigen (SEA) to facilitate targeting of $G_{D2}$ producing cells.

Direct conjugation of scFv or scFv-streptavidin to toxin replaces the cell-binding domain of natural toxins with the scFv, which serves as a tumor binding domain specific to $G_{D2}$ expressing cells. ScFv-ricin-A-chain and scFv-pseudomonas toxin have been successfully constructed for other scFv. This coupling is advantageously performed at the DNA level, not at the protein level. For example, when the fusion protein of the heavy chain, the light chain and the linker is created by overlap PCR extension, a DNA coding for the toxin can also included, and then expressed along with the scFv.

scFv and scFv-streptavidin can also be usefully combined in a fusion protein with CD8. scFv-CD8 constructs can be transfected through retroviral vector into human and mouse lymphocytes. Since these scFv are permanently integrated into the cellular genome, these lymphocytes express scFv on their cell surface and through the CD8 cytoplasmic domain become activated upon antigen binding. scFv facilitates the homing of these cells to tumor sites, thus being effective in promoting both the localization and killing of tumors. With a suicide gene, thymidine kinase, also transfected, these cells can now be turned on and off as needed.

scFv-enzyme and scFv-enzyme-streptavidin conjugates can be used to provide targeted drug therapy using a technique known as ADEPT (antibody directed enzyme prodrug-therapy). Suitable enzymes for this technique include carboxypeptidase G2, alkaline phosphatase, and β-Lactamase. A prodrug derivative (e.g. cephalosporin derivative of doxo20) becomes activated to the active agent by the enzyme (beta-lactamase) targeted to the tumor by the scFv. Thus tumor cells are exposed to a high local concentration (up to 10-fold higher than blood/tissue levels) of specific chemotherapeutic agents.

Integration of scFv (with or without streptavidin) into viral coat proteins can be used to retarget these viruses in vivo. These viruses include adenovirus, retrovirus and herpes virus.

Superantigen (SEA) can stimulate T cells without the requirement of MHC.21 ScFv-SEA and scFv-streptavidin-SEA can target T cells to lyse antigen-positive MHC-class II-negative human tumor cells. SEA has been cloned (Betley et al: J. Bacteriology 170: 34–41, 1988) and the cDNA is available for making fusion proteins.

EXAMPLE 1

5F11 hybridoma cells were processed for mRNA using a commercially available kit (Quick Prep Micro mRNA Purification, pharmacia Biotech) following the procedures outlined by the manufacturer. Briefly, hybridoma cells were cultured in ROPMI-1640 medium supplemented with 10% calf serum, 2 mmol/L L-glutamine (Sigma), 100 U/L penicillin and 100 ug/ml streptomycin sulfate (Sigma). The cell cultures were maintained at 37° C. under a water-saturated atmosphere of 5% $CO_2$. $5 \times 10^6$ cells were pelleted by centrifugation at 800 g and washed once with RNase-free phosphate buffered saline (pH 7.4), The recentrifuged cells were lysed directly in the extraction buffer. Poly(A)+RNA was purified by a single fractionation of oligo(dT)-cellulose and then eluted with elution buffer. The mRNA sample was precipitated for 1 hour at 100 ug glycogen, 40 ul of 2M potassium acetate and 1 ml absolute ethanol at −20° C. The nucleic acids were recovered by centrifugation at 10,000 g for 30 minutes, The sample was evaporated until dry and dissolved in 20 ul RNase-free water.

The mRNA preparation was used in the construction of the 5F11 scFv gene using the Mouse ScFv Module/Recombinant Phage Antibody System (Pharmacia Biotech). 5 ul of the mRNA preparation was reverse transcribed in a total volume of 11 ul of reaction mixture and 1 ul DTT solution for 1 hour at 37° C. For PCR amplification of immunoglobulin variable region, light primer mix and the heavy primer set were added respectively to generate quantities of the light (325 bp(and heavy (340 bp) chains. Following an initial 5 minute dwell at 95° C., 5 U Ampli Taq DNA polymerase (Perkin Elmer) was added. The PCR cycle consisted of a 1 min denaturation step at 94° C., a 2 min. annealing step at 55° C. and a 2 min extension step at 72° C. After 30 cycles of amplification, PCR derived fragments were purified using glassmilk beads (Bio 101 Co.) and evaluated by electrophoresis on 1/5% agarose gel in TAE buffer with ethidium bromide visiualization. For the assembly and fill-in reaction, both purified heavy chain and light chain fragments were added to ab appropriate PCR mixture containing linker-primer, dNTPs, PCR buffer and Ampli Taq DNA polymerase. Denaturation was performed at 94° C. for 1 minute, followed by a 4 minute annealing reaction at 63° C. The heavy and light DNA were joined into a single chain with linker DNA after 7 thermocycles. Using this single chain DNA as a template and restriction site primers (RS primers) containing either SfiI or NotI restriction sites, secondary PCR amplification was carried out for 30 cycles to amplify the ScFv DNA and add the restriction sites. This introduced the SfiI restrictions site at the 5'-end of the heavy chain and the NotI restriction site at the 3'-end of the light chain. Amplified ScFv DNA was then purified by glassmilk beads and digested with SfiI and NotI.

Purified scFv DNA was inserted into the pCantab 5e vector (Pharmacia Biotech) by ligation as SfiI/NotI sites in the vector. Competent E. Coli XL 1-Blue cells were transformed with pCantab 5E phagemid containing the ScFv DNA following the method outlined in Stratagene protocols. For rescue of a recombinant phage antibody library, the helper phage M13 K07 was added.

Antibody-producing recombinant phage were selected by panning using the method of Ditzel, PNAS USA 91: 3710–3714 (1994) with slight modifications. 20 ul of GD2 (1 ul/ml) dissolved in ethanol were directly coated on a 96-well polystyrene plate and dried at rom temperature. Then 100 ul of the supernatant containing the phage library was added to each well and incubated for 2 hours. The plate was then washed 10 times with PBS containing 0.05% BSA to remove nonspecifically bound phage. Antibody-positive recombinant phage captured by the GD2 antigen was eluted with 0.1 M HCl (pH 2.2 with solid glycine and 0.1% BSA) and neutralized with 2M Tris solution. Selected phage was then re-panned for two additional cycles to further enrich the GD2-binding recombinant phages.

The selected phage was used to reinfect E coli XL1-Blue cells. Clones were grown in 2XYT medium containing ampicillin (100 ug/ml) and 1% glucose at 30° C. until an OD600 of 0.5 was obtained. Expression of ScFv antibody was induced by changing to a medium containing 100 uM IPTG and incubating overnight at 300° C. The supernatant obtained from the medium by centrifugation was directly added to a plate coated with GD2. The pellet was resuspended in PBD containing 1 mM EDTA and incubated on ice for 10 minutes. The periplasmic soluble antibody was collected by centrifugation again and added to the plate. After incubating at 37° C. for 32 hours, anti-E Tag antibody (Pharmacia Biotech) was used to specifically screen the binding of the ScFv fragment.

For construction of the 5FpoStMCH vector which contains the 5F11-scFV-streptavidin plasmid DNA, plasmid DNA from the 5F11-scFv in pCantab 5E vector (Pharmacia Biotech) was purified and amplified by PCR using two specially designed primers S6 and 318s. S6 contains a NotI restriction site and 318s contains a PvuII restriction site so that amplified DNA can be restriction digested and inserted in the pSTE vector (Dr. Dubel, German Cancer Center). The resulting vector 5FpoStMCH is the 5F11-scFv-streptavidin construct. The streptavidin was digested with BamHI, leaving the scFV 5FpoMCH.

EXAMPLE 2

Supernatant, periplasmic extract and cell extract from positive clones were fractionated on unreduced SDS-PAGE 12% SDS-polyacrylamide slab gels and buffer prepared according to Laemmli (1970). Electrophoresis was performed at 100V for 45 min. After completion of the run, western blot analysis was carried out as described by Towbin (1979). The nitrocellulose membranes were blocked by 1% nonfat milk in TBS solution for 1 hour and incubated with anti-E Tag antibody for 1 hour at room temperature. After incubating with HRP-conjugated goat anti-mouse Ig (Fisher Co.), the membrane was detected by ECL System (Amersham). The results showed a protein band with an apparent molecular mass of 31KD using anti-E Tag antibody which recognizes the sequence GAPVPVPDPLEPR (SEQ. ID. NO.5). The same protein was not detected in control cells nor in cells without IPTG treatment to induce expression of the scFV.

EXAMPLE 3

Immunostaining thin layer chromatography was performed under conditions similar to those described by Tai et al (1987). GD2, GD3, GD1a, GD1b, GM2, GT1b and GL1000 were dissolved in ethanol and spotted on an HPTLC plate. The supernatant from ScFv 5F11 clone and 5F11 hybridoma cells were incubated with the spread plate. Immunostaining was visualized with the use of o-phenylenediamine dihydrochloride (Sigma). GD2 antigen was detected by both the ScFv supernatant and the 5F11 Mab, which appeared similar in specificity. Cross-reactions of the ScFv antibody with other glycolipids was not detected.

EXAMPLE 4

In constructing 3G6-scFv, the orientation VH-VL did not produce a functional scFV. Therefore the orientation VL-VH was used. cDNA of VH and VL of 3G6 hybridoma were linked through a custom built linker and inserted into the pHEN vector (DR. Greg Winter). NcoI and NotI restriction sites were built into the VH and VL linkers so that the scFV can be digested with these enzymes for insertion in the pSTE vector. Clone 7 was chosen and called 3GpoStMCH. Digestion of the streptavidin position of the gene left behind 3G6-scFv, now called 3GpoMCH. The following references are cited above, and are incorporated herein by reference.
1. Rodden F A, Wiegandt H, Bauer B L: Gangliosides: the relevance of current research to neurosurgery. J Neurosurg 74:606–619, 1991
2. Berra B, Gaini S M, Riboni L: Correlation between ganglioside distribution and histological grading of human astrocytoma. Int J Cancer 36:363–366, 1985
3. Traylor T D, Hogan E L: Gangliosides of human cerebral astrocytomas. J Neurochem 34:126–131, 1980
4. Ye J N, Cheung N K V: A novel O-acetylated ganglioside detected by anti-$G_{D2}$ monoclonal antibodies. Int J Cancer 50:197–201, 1992
5. Wikstrand C J, Fredman P, Svennerholm L, et al: Expression of gangliosides GM2, $G_{D2}$, GD3, 3'-sioLM1, and 3',6' isoLD1 in CNS malignancies as defined by epitope-characterized monoclonal antibodies (Mabs). 9th International Conference on Brain Tumors Research and Therapy 1991 (abstract)
6. Longee D C, Wikstrand C J, Mansson J E, et al: Disialoganglioside $G_{D2}$ in human neuroectodermal tumor cell lines and gliomas. Acta-Neuropathology (Berl) 82:45–54, 1991
7. Hoon D S, Banez M, Okun E, et al: Modulation of human melanoma cells by interleukin-4 and in combination with gamma-interferon or alpha-tumor necrosis factor. Cancer Res 51:2002–2008, 1991
8. Arbit E, Yeh S J, Cheung N K, Larson S M: Quantitative Immunoimaging of gliomas in humans with anti-ganglioside monoclonal antibodies. J Neurosurg 76:399a, 1991
9. Saito M, Yu R K, Cheung N K V: Ganglioside $G_{D2}$ specificity of monoclonal antibodies to human neuroblastoma cell. Biochem Biophys Res Comm 127:14, 1985
10. Lammie G A, Cheung N K V, Gerald W, et al: Ganglioside $G_{D2}$ expression in the human nervous system and in neuroblastomas—an immunohistochemical study. Int J Oncol 3:909–915, 1993
11. Sariola H, Terava H, Rapola J, Saarinen U M: Cell-Surface Ganglioside $G_{D2}$ in the Immunohistochemical Detection and Differential Diagnosis of Neuroblastoma. AJCP 96:248–252, 1991
12. Saarinen U M, Sariola H, Hovi L: Recurrent Disseminated Retinoblastoma Treated by High-dose Chemotherapy, Total Body Irradiation, and Autologous Bone Marrow Rescue. Am J Pediatr Hematol/Oncol 13:315–319, 1991
13. Heiner J, Miraldi F D, Kallick S, et al: In vivo targeting of $G_{D2}$ specific monoclonal antibody in human osteogenic sarcoma xenografts. Cancer Res 47:5377–5381, 1987
14. Chang H R, Cordon-Cardo C, Houghton A N, et al: Expression of disialogangliosides $G_{D2}$ and GD3 by human soft tissue sarcomas. Cancer 70:633–638, 1992
15. Cheung N K, Neely J E, Landmeier B, et al: Targeting of ganglioside $G_{D2}$ monoclonal antibody to neuroblastoma. J Nucl Med 28:1577–1583, 1987
16. Yeh S D, Larson S M, Burch L, et al: Radioimmunodetection of neuroblastoma with iodine-131-3F8: Correlation with biopsy, iodine-131-Metaiodobenzylguanidine (MIBG) and standard diagnostic modalities. J Nucl Med 32:769–776, 1991
17. Miraldi F D, Nelson A D, Kraly C, et al: Diagnostic imaging of human neuroblastoma with radiolabeled antibody. Radiology 161:413–418, 1986
18. Grant S C, Kostakoglu L, Kris M G, et al: Imaging of small cell lung carcinoma with the monoclonal antibody 3F8. Proc Am Soc Clin Oncol 10:265, 1991 (abstract)
19. Yeh S D J, Casper E S, Cheung N K V, et al: Radioimmunoimaging of soft-tissue sarcoma with an anti-ganglioside monoclonal antibody 3F8. 5th Asia & Oceania Cong of Nucl Med & Biol Proceedings: 104, 1992
20. Svenson H P, Vrudhula V M, Emswiler J E, et al: In Vitro and In Vivo Activities of a Doxorubicin Prodrug in Combination with Monoclonal Antibody β-Lactamase Conjugates. Cancer Res 55:2357–65, 1995
21. Dohisten M, Abrahmsen L, Bjork P, et al: Monoclonal antibody-superantigen fusion proteins:Tumor-specific agents for T-cell-based tumor therapy. Proc Natl Acad Sci (USA) 91:8945–8949, 1994
22. Dhingra K, Fritsch H, Murray J L, et al: Phase I Clinical and Pharmacological Study of Suppression of Human Antimouse Antibody Response to Monoclonal antibody L6 by Deosxysspergulin. Cancer Res 55:3060–67, 1995
23. Wnag C-Y, Huang L: p-H-sensitive immunoliposomes mediate target-cell-specific delivery and controlled expression of a foreign gene in mouse. Proc Natl Acad Sci (USA) 84:7851–55, 1987
24. Vieweg J, Boczkowski D, Roberson K M, et al: Efficient Gene Transfer with Adeno-associated Virus-based Plasmids Complexed to Cationic Liposomes for Gene Therapy of Human Prostate Cancer. Cancer Res 55:2366–2372, 1995
25. Lorimer I A J, Wikstrand C J, Batra S K, et al: Immunotixins That Target an Oncogenic Mutant Euidermal Growth Factor Receptor Expressed in Human Tumors. Clin Can Res 1:859–64, 1995

What is claimed is:

1. A recombinant polynucleotide encoding a single chain anti-$G_{D2}$ antibody, said polynucleotide comprising a region encoding the variable region of the light chain of an anti-$G_{D2}$ antibody linked to a region encoding the variable region of the heavy chain of an anti-$G_{D2}$ antibody, wherein the variable region of the light chain is linked to the variable region of the heavy chain in an orientation whereby a peptide expressed from the polynucleotide binds to $G_{D2}$, and wherein the polynucleotide comprises, in contiguous sequence, the bases identified in SEQ. ID NO: 2.

2. A recombinant polynucleotide encoding a single chain anti-$G_{D2}$ antibody, said polynucleotide comprising a region encoding the variable region of the light chain of an anti-$G_{D2}$ antibody linked to a region encoding the variable region of the heavy chain of an anti-$G_{D2}$ antibody, wherein the variable region of the light chain is linked to the variable region of the heavy chain in an orientation whereby a peptide expressed from the polynucleotide binds to $G_{D2}$, and wherein the polynucleotide comprises, in contiguous sequence, the bases identified in SEQ. ID NO: 1.

3. The polypeptide of claim 2, further comprising a region encoding an additional protein.

4. The recombinant polynucleotide of claim 3, wherein the additional protein is streptavidin.

5. The recombinant polynucleotide of claim 3, wherein the additional protein is a pro-drug converting enzyme.

6. The polypeptide of claim 1, further comprising a region encoding an additional protein.

7. The recombinant polynucleotide of claim 6, wherein the additional protein is streptavidin.

8. The recombinant polynucleotide of claim 6, wherein the additional protein is a pro-drug converting enzyme.

* * * * *

UNITED STATES PATENT AND TRADEMARK OFFICE
CERTIFICATE OF CORRECTION

| | |
|---|---|
| PATENT NO. | : 6,451,995 B1 |
| APPLICATION NO. | : 09/142974 |
| DATED | : September 17, 2002 |
| INVENTOR(S) | : Cheung et al. |

It is certified that error appears in the above-identified patent and that said Letters Patent is hereby corrected as shown below:

Column 1, Line 13: This application was supported by DOE grant number DE-FG02-93ER61658. The US government has certain rights in this invention.

Signed and Sealed this

Twenty-fifth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 6,451,995 B1  Page 1 of 1
APPLICATION NO. : 09/142974
DATED : September 17, 2002
INVENTOR(S) : Cheung et al.

It is certified that error appears in the above-identified patent and that said Letters Patent is hereby corrected as shown below:

Column 1, Line 13: insert This application was supported by DOE grant number DE-FG02-93ER61658. The US government has certain rights in this invention.

Signed and Sealed this

Fifteenth Day of January, 2008

JON W. DUDAS
*Director of the United States Patent and Trademark Office*